US00PP11165P

United States Patent [19]

Morrison

[11] Patent Number: Plant 11,165

[45] Date of Patent: Dec. 28, 1999

[54] HIBISCUS PLANT NAMED 'MORRISON-GILBERG (IV)'

[75] Inventor: William L. Morrison, Park Ridge, Ill.

[73] Assignee: Gilberg Perennial Farms, Inc., Glencoe, Mo.

[21] Appl. No.: 09/008,447

[22] Filed: Jan. 16, 1998

[51] Int. Cl.[6] ..... A01H 5/00

[52] U.S. Cl. ..... Plt./257

[58] Field of Search ..... Plt./67.8, 257

[56] References Cited

U.S. PATENT DOCUMENTS

P.P. 9,838 3/1997 Bost ..... Plt./257

*Primary Examiner*—Howard J. Locker
*Assistant Examiner*—Kent L. Bell
*Attorney, Agent, or Firm*—Howell & Haferkamp, L.C.

[57] ABSTRACT

A new and distinct hybrid variety of *Hibiscus moscheutos*, particularly distinguished by having flowers of from seven to twelve inches in diameter that are light fuschia with a darker eye, closely matching Pantone 224U with a Pantone 227U eye and with fully overlapping petals. The blooming period is about 3 to 4 weeks, but individual blooms allowed to remain on the plant typically last about 2 days. Mature plant specimens are about 3½ to 5½ feet in height. The distinguishing characteristics are constant and stable in asexually reproduced plants.

2 Drawing Sheets

BACKGROUND OF THE INVENTION

The present invention relates to a new and distinct variety of herbaceous perennial, more particularly to a hybrid variety of hibiscus.

BRIEF SUMMARY OF THE INVENTION

The new cultivar was developed by me as a progeny by cross-pollination in a garden in Park Ridge, Ill., a suburb of Chicago. The plant was originally produced as a seedling and has been successfully asexually reproduced by root crown division, under casual backyard gardening conditions. The plant has also been reproduced by vegetative reproduction, i.e., by tip and stem cuttings. The original seedling had parentage of 'White and Light Pink' (unpatented) pollen parent and 'Giant Crimson Red' (unpatented) seed parent, both of which are cultivars of *Hibiscus moscheutos* grown and named by the inventor. The present cultivar is a herbaceous perennial; the stalks die back to ground level every winter and new stalks emerge in late spring. The trade name "MAUNA LOA PINK" has been coined for this cultivar, although the cultivar was neither marketed nor was its existence made public prior to the filing of the present U.S. Plant Pat. application. The present cultivar is distinguished by having flowers of from seven to twelve inches in diameter. These unusually large flowers can be cut and used for centerpiece displays, and last equally long with or without water. By comparison, *Hibiscus rosa-sinensis* (Chinese Hibiscus Rose of China) flowers are two to six inches in diameter, and *Hibiscus syriacus* (Rose-of-Sharon or Althea) flowers are three to six inches in diameter. In its natural growth habit in the Chicago area, the present cultivar may be distinguished from both its pollen parent 'White and Light Pink' and its seed parent 'Giant Crimson Red' in that the flowers are larger than those of either parent. Most typically, the present cultivar has flowers seven to twelve inches in diameter, as compared to 8–10 for 'White and Light Pink' and 9–10 for 'Giant Crimson Red'. Mature specimens of the present cultivar are also smaller than either parent, most typically being about 3½ to 5½ feet in height, as compared to 5 to 6 feet in height for 'White and Light Pink' and 7 to 8 feet in height for 'Giant Crimson Red'. The length of the blooming period is also about one week longer for the present cultivar than for 'White and Light Pink'. The most significant difference, however, is that the present cultivar has flat, fully overlapping petals that hold their shape, whereas neither parent has fully overlapping petals. The greatest number of flowers for the present cultivar was obtained in environments of half to full sun. The largest flowers were obtained at summer temperatures from 70 to 100 degrees Fahrenheit. Smaller flowers were observed to bloom at temperatures as low as 50 to 60 degrees Fahrenheit. Reproduction by root crown division consistently produces plants with identical, stable characteristics. A further botanical description of the new variety follows. Distinguishing color characteristics are listed on the attached Plant Color Coding Sheet. The distinguishing characteristics listed thereon should not necessarily be assumed to be exhaustive. Although the listed characteristics are believed to be the primary distinguishing color characteristics of the cultivar, it is possible that others may become evident upon further observation and comparison with other cultivars. These descriptions were made from specimens reproduced and grown under casual backyard gardening conditions in suburban Chicago, Ill., and from specimens grown under greenhouse and outdoor gardening conditions in suburban St. Louis, Mo. Except as noted, no differences were observed between the two locations, except that specimens were observed to grow somewhat faster and the blooming period is somewhat longer under warmer conditions, as one might expect for plant specimens of this species. In the following description, color references are made to the Pantone Color Product Selector (© 1989 Pantone) except where general terms of ordinary significance are used.

BRIEF DESCRIPTION OF THE DRAWINGS

The accompanying drawings clearly depict the new variety, showing the colors as true as it is reasonably possible to obtain in colored reproductions of this type. Actual flower, leaf, sepal, and bud colors may differ from flower, leaf, sepal, and bud colors in the photographs due to light reflectance.

DETAILED BOTANICAL DESCRIPTION

Figure 1:
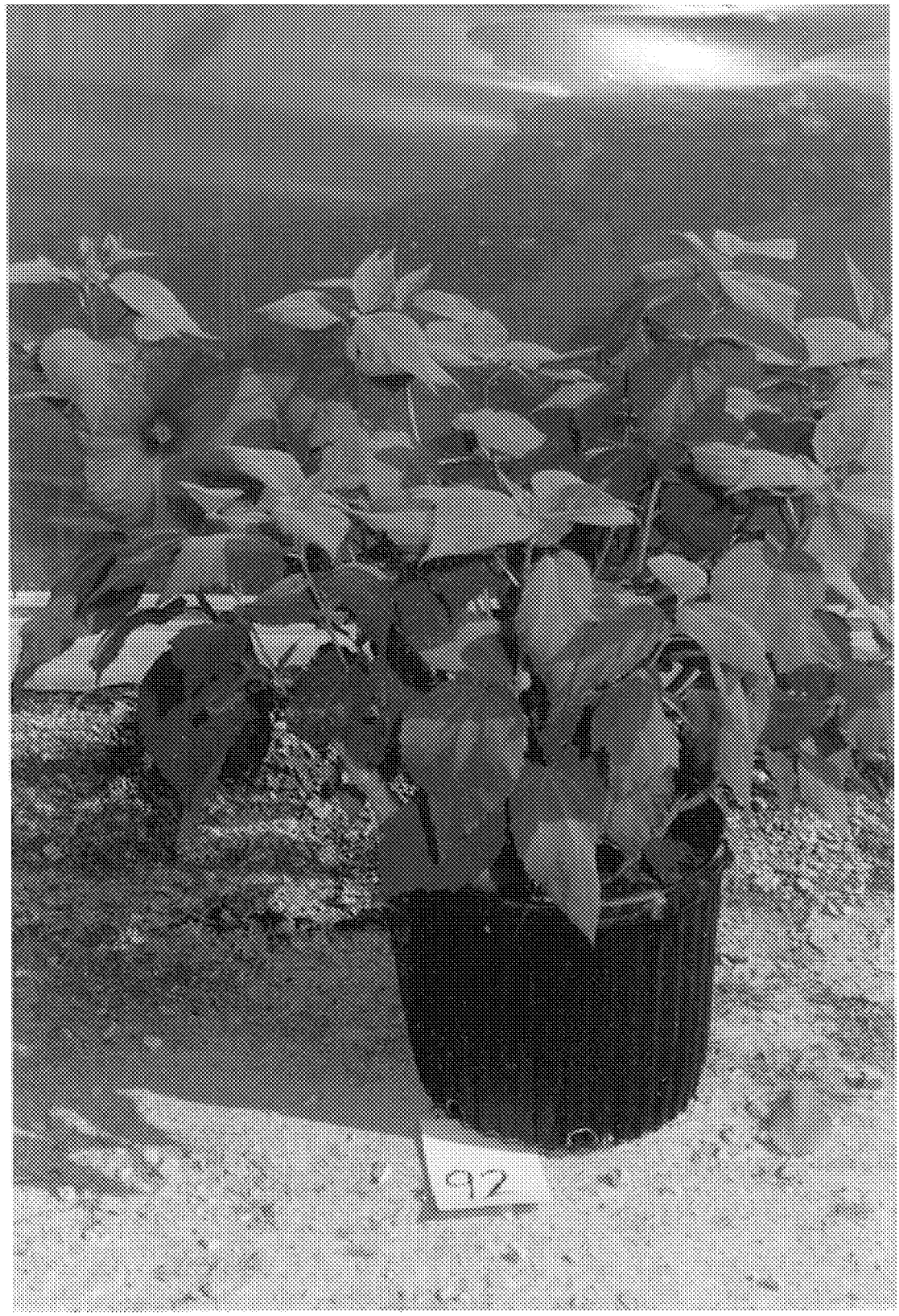
FIG. 1 depicts a side view of the *Hibiscus moscheutos*, 'Morrison-Gilberg (IV)' cultivar of the present invention.
Figure 2:
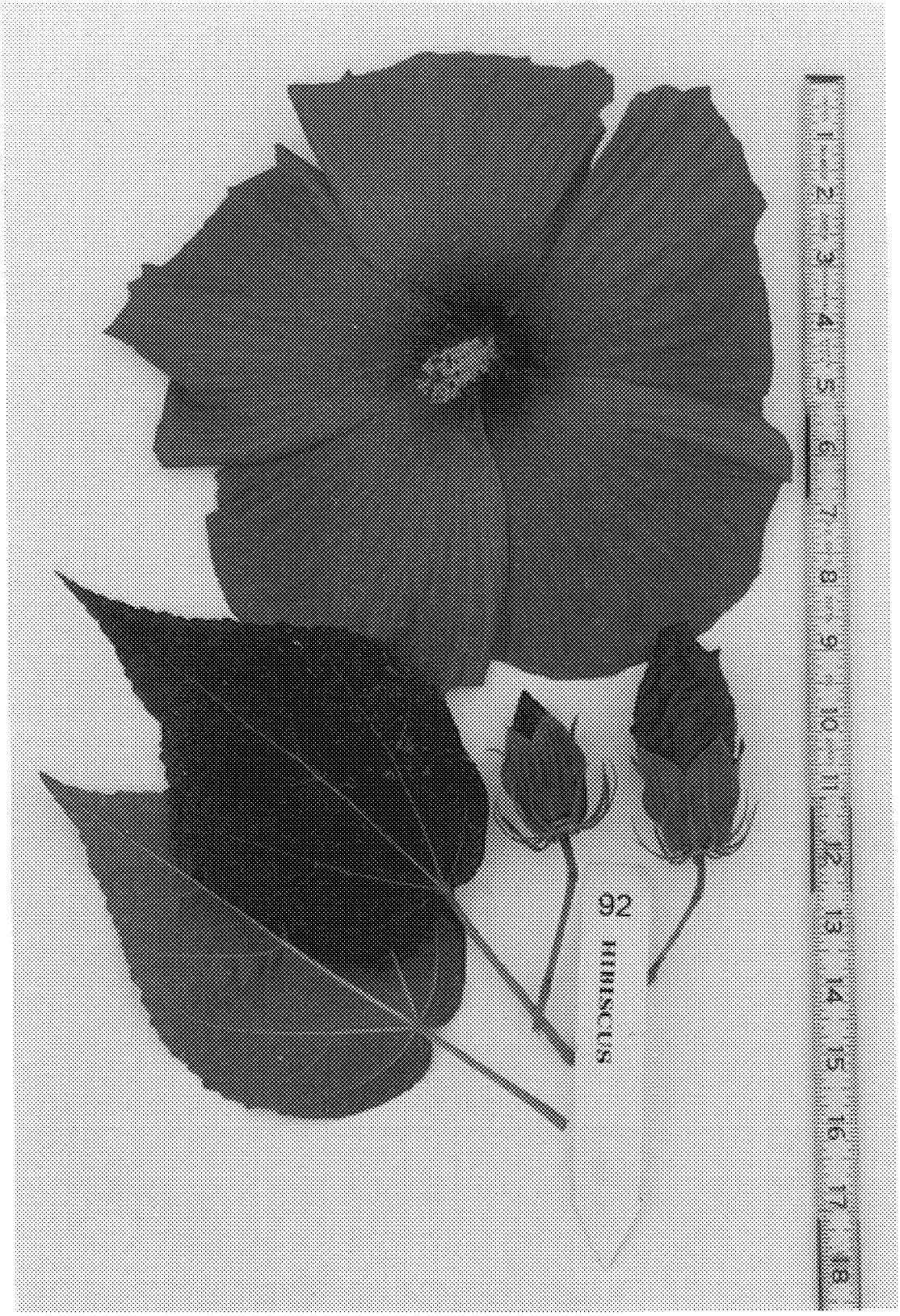
FIG. 2 is a close-up view of freshly cut portions of the *Hibiscus moscheutos*, 'Morrison-Gilberg (IV)' cultivar of the present invention, showing the flower, leaves, and sepals surrounding flower buds in great detail.

Form: Numerous stalks grow upright from perennial roots.

Habit: Individual stalks with many leaves uniformly distributed on the stalks and numerous flowers bloom continuously. Rapid and strong stalk growth have flowers facing outward.

Productivity: Produces continous new flower displays, vigorous and profuse.

Precocity: Elegant displays of flowers, each stalk displaying one new flower after another. On each stalk, as one flower closes and its petals fall off, a flower next to it and closer to the top of the stalk blooms, so that the displays appear to be continuous. The display periods may vary depending upon climate and the vigor of particular specimens.

Stalks: Mature presentations occur the first year. Strong and smooth skin covered, and hold many leaves and flowers securely. Staking is typically not required under normal full sun growing conditions. However, specimens grown in shaded sunlight produce stalks that are softer and that may require staking. New stalks emerge in May.

Temperature: Winter hardy during freezing winters. On 100 degree (Fahrenheit) days, the flowers bloom equally as they do during a mild day.

Insects: Negligible insect damage has occurred to date in any individual plant, even though no pesticides have been used, and no slugs have been observed on the plants.

Animals: Rodents, rabbits and squirrels have not been observed to bother the stalks or roots.

Rooting: The plants root easily without fertilizer and send out their roots quickly and securely.

Foliage: Large leaves evenly distributed vertically and horizontally on the stalks.

Leaves: Abundant and decorative in alternate order. Medium to dark green leaves with margin lengths of from three to eight inches in elongated heart form. Typical leaves are 6½" long by about 3 to 3½" wide at the base. Top color is Pantone 3435U, bottom is Pantone 556U. Shape is cordate, with crenulated margins. Leaf tips are apiculate, bases are cordate, and venation is pinnate. Texture is matte. Petioles from two to four and one-half inches. No stipules.

Petide color: Lighter green than the leaves, with some dusted rust color. Height: Mature plants ar efrom three to five and one-half feet in height.

Shape of plant at maturity: Rounded, almost globe-shaped.

The Flowers

Buds: Shaped like a pointed egg and very large one to two days before blooming. Very large, can be over 3" in length. A typical bud measures about 3¾" in length by about 1½" at its widest point. Color is Pantone 215U.

Blooming habit: Continuous and free blooming.

Petals: Two to six inches long, five per flower.

Diameter of flower: A distinguishing feature of the variety, flowers are from seven to twelve inches in diameter.

Shape: Circular and relatively flat with overlapping petals.

Number of flowers: Approximately 10–15 flowers per stalk in mature plants, with essentially flat appearance. Can be changed substantially by cutting back main stem, and further by cutting back secondary stems for more flowers on the plant.

Filaments: Each of the approximately 15 filaments attaches to the large style projecting from the center of the flower. Approximately ⅛" to ¼" in length.

Stamens: Pink, very numerous, extending from the style.

Pistil: Two to five inches long and yellow, with the stamen and stigma attached.

Stigma: Pink, with five pollen receptors.

Style: Pink. About two inches long and supports the stigma.

Pollen: Yellow and plentiful.

Shape of petal: Overlapping and broadly obovate (almost reniform) recurved at the base to form a small green star of revealed calyx, with overall circular shape.

Texture: Central one-fourth satiny; outer three-fourths velvety.

Aspect: Like fine kidskin in appearance and strongly self-supporting.

Color: Light fuschia with darker eye, closely matching Pantone 224U with Pantone 227U eye. Constant and stable in asexually reproduced plants.

Calyx: Six sepals, medium green color.

Bractlets: About 1½" medium green.

Blooming period: Mid summer to frost with continuous color presentation. In suburban Chicago, the blooming period typically lasts from the first part of August into September, or about 3 to 4 weeks. Container plants produce flowers longer, on lateral stems, as the main stems are cut back and laterals emerge.

Lastingness of the Bloom: Individual blooms allowed to remain on the plant last approximately 1–3 days per bloom, typically two full days. Individual flowers hold their shape for about a day after cutting with about 2 to 3 inches of stem, with or without water, if not exposed to wind and heat, which can cause them to wilt and fade quickly. However, if buds almost ready to open are cut with about one foot of stem, the cuttings may be kept in water for 1–3 days and will open almost normally.

Penducle: Two to four inch stiff pedicels (color Pantone 556U) to support the flower during blooming and the seed pod formation later.

Fruit: Seeds produced, typical of the species.

Fragrance: Minimal.

Disease resistance: No disease problems have been noted on stalks, leaves or flowers.

Environmental Conditions: The plants can stand drought or up to two inches of rainwater without adverse effects.

Winter dormancy: The plants lose their leaves at frost and stems die back to ground level.

Fertility: Midwest topsoil provides adequate nutrients without additional fertilizer.

Regularity of bearing: Consistent year-to-year flowering has been observed.

What is claimed is:

1. A new and distinct variety of *Hibiscus moscheutos* plant, as herein shown and described.

* * * * *